US00PP08537P

United States Patent [19]

Hefner

[11] Patent Number: Plant 8,537

[45] Date of Patent: Jan. 11, 1994

[54] HOLLY TREE NAMED ILEX×'HEFCUP'

[76] Inventor: Randy B. Hefner, Rte. 4, Box 520, Conover, N.C. 28613

[21] Appl. No.: 863,691

[22] Filed: Apr. 2, 1992

[51] Int. Cl.[5] ..... A01H 5/00
[52] U.S. Cl. ..... Plt./65
[58] Field of Search ..... Plt. 65

[56] References Cited

PUBLICATIONS

Dirr, M. A. 1990, Manual of Woody Landscape Plants, 4th ed. Stipes Publ. Co., Champaign, Ill. pp. 417–418.
Liberty Hyde Baily Hortorium, 1976 Hortus Third: A Concise Dictionary of Plants Cultivated in the U.S. & Canada, MacMillan Publ. Co. New York, N.Y. p. 589.

*Primary Examiner*—James R. Feyrer
*Assistant Examiner*—Erich Veitenheimer

[57] ABSTRACT

A new and distinct selection of *Ilex aquifolium* X cornuta shrub herein referred to as Ilex×'Hefcup'. A sport selection characterized from the plant it was discovered on (Ilex×'Nellie R. Stevens') by its distinct yellow variegated leaves. The form of variegation ranges from yellow margins on some leaves to laminated golden variegations on others with the remaining leaves being predominantly solid golden-yellow. All first year leaves exhibit one or more of these forms. The new selection produces female flowers and large yellow berries during the summer which ripen red in the fall.

8 Drawing Sheets

DISCOVERY

Ilex×'Hefcup' is a new and distinct, variegated female cultiver discovered by Randy Hefner in June 1978, as a variegated sport of Ilex×' Nellie R. Stevens' growing on an individual plant in Hefner's Nursery, Conover, N.C. 'Hefcup' to date is known to exist only within the boundaries of Hefner's Nursery and has not been offered for sale or described in any publication. The origin of the cultivar name (a combination of the first part of the owner's last name and the last part of buttercup) was derived by Randy Hefner for the fanciful resemblance of the yellowish color of first year foliage of this new distinct cultivar to the flowers of buttercups (Ranunculus spp.).

The parent 'Nellie R. Stevens' is a selection of the putitive hybrid between *Ilex aquifolium*×*Ilex cornuta* (Liberty Hyde Bailey Hortorium 1976; Dirr 1990) released by G. A. VanLennep. Jr., St. Michael, Md. in 1954 and named after its owner, Nellie R. Stevens, Oxford, Md. (Dirr 1990). An epithet for this hybrid cross is unknown. Therefore, nomenclature of the new cultivar Ilex×'Hefcup' follows the standard practice used for the parent.

REPRODUCTION

Ilex×'Hefcup' has been strictly reproduced asexually at Hefner's Nursery by vegetative cuttings to preserve the genetic attributes that make it different from the parent 'Nellie R. Stevens'. The potential loss of these genetic attributes in sexual reproduction prohibits propagation by seed. Seed progeny of Ilex×'Hefcup' had not been observed.

Since its discovery in 1978, five generations of progeny have been reproduced by vegetative cuttings using conventional mist propagation without difficulty. It has been noted that cuttings with solid yellow leaves tend to produce progeny which also produce predominantly solid yellow foliage, with the remaining foliage of the more typical variegation. All cuttings of each distinct variegation form produce progeny exhibiting all of the other variegation forms as well. Ilex×'Hefcup' has never "reverted" or produced green foliage on first year growth.

CHARACTERISTICS

This new selection differs from the parent 'Nellie R. Stevens' by the unique genetic attributes of leaf color patterns and fruit color. Our new selection has a variegated leaf pattern. New growth often exhibits a bronze to peach-yellow color upon emergence. Leaves on first year growth are either solidly buttercup yellow or variegated. The variegated leaves comprise predominantly two primary colors, a golden hue which generally extends inwardly from the margins of the leaves, but may also be expressed medially and interveinal between the prominent lateral veins, and a deep green color which usually is expressed in the central portion of the leaves. The patterns formed are characteristically different from leaf to leaf, and are thought to derive from two or more genetically distinct histogenic regions of the leaf forming meristem, and are thought to represent a "hand-in-glove" type of chimera. The leaf cells formed from each region differ in chlorophyll content; resulting in differences in coloration. Due to differences in speed of growth, the tissue formed by each respective region will develop into varied patterns relative to the other; giving different expressions in leaf mesophyll layers and the pallisade cell layer. This results in different patterns determined by the area of each layer occupied by cells of each genotype. Where one or more layers of cells of golden color overlay a layer of green cells, intermediate colors are displayed at the leaf surface and the leaf takes on a laminated appearance. Because more than one layer of mesophyll cells may develop from a different meristematic region, one, two, or more layers of golden-colored cells may mask the green of underlying cells of a lower cell layer, and the lamination may look several layers deep and result in two or more intermediate colors of different shades.

Plants grown in full sunlight exhibit the typical golden variegated foliage whereas those grown in shade exhibit leaves with a laminated green variegation. Leaf variegation fades with age; thus, plants exhibit a dark green interior with a golden exterior, a very ornamental appearance as one moves away from a planting.

Fruits of 'Hefcup' are red, similar to 'Nellie R. Stevens' when ripe. 'Hefcup' is distinctive in bearing yellowish fruits during the summer when the fruits are expanding.

'Hefcup' has been observed to exhibit the following: (1) Plants exhibit a pyramidal growth form similar to 'Nellie R. Stevens', and should reach a mature size of 18–20' high by 8' wide; (2) 'Hefcup' grows slower in field culture than 'Nellie R. Stevens', but at an equivalent rate in container production; (3) Variegation is best when 'Hefcup' is produced under optimum conditions; (4) Severe conditions such as drought and colder winter conditions resulted in some leaf burn on leaves that were predominantly yellowish; (5) New leaves exhibit a bronze to peach-yellow color as they emerge; (6) Variegation occurs on all leaves during the first season of growth; (7) Leaf variegation fades as more green appears during the second growing season, with sun exposed leaves exhibiting more golden hues towards the apex and margin; (8) Leaf variegation becomes more greenish during the third growing season, yet many of these inner leaves exhibit a laminated green appearance up close.

DESCRIPTION OF DRAWINGS

Distinguishing characteristics of Ilex×'Hefcup' are illustrated in the accompanying color photographic drawings.

DESCRIPTION

Figure 1:
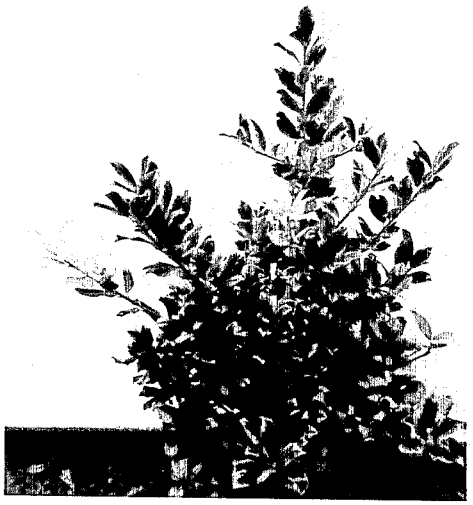
FIG. 1 shows a six-year-old fourth generation progeny growing in a nursery field exhibiting the typical range of variegations.
Figure 2:
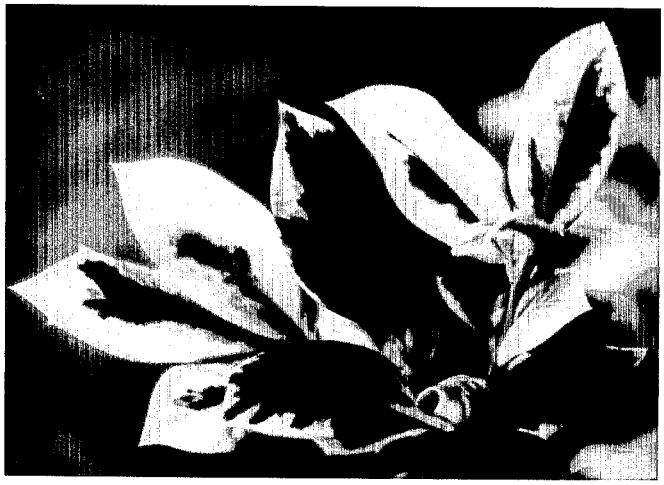
FIGS. 2 and 3 are close-ups of first year foliage showing marginated and laminated variegations as as well as solid buttercup yellow leaves. Note different shades of variegation in the laminated leaf centers.
Figure 3:
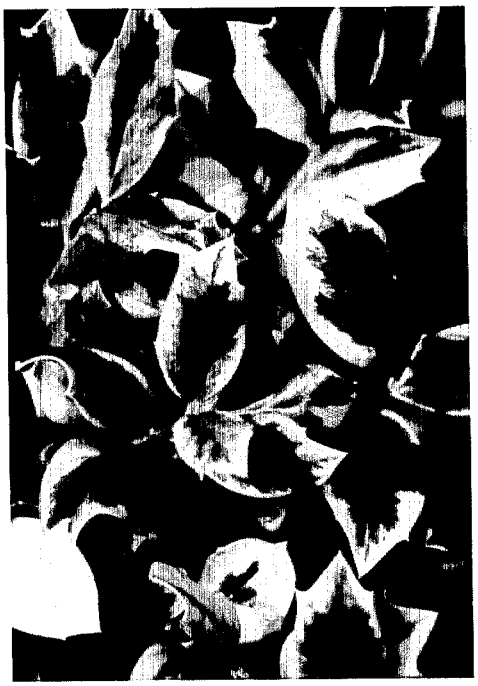
Figure 4:
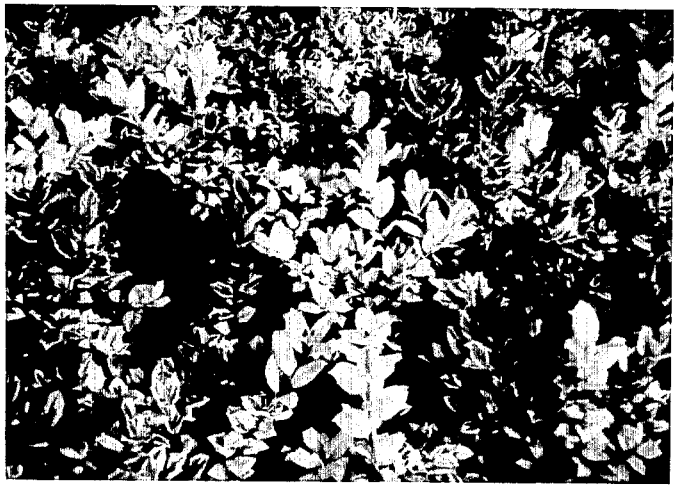
FIG. 4 shows a group of three-year-old progeny growing in three quart containers which were propagated from third, fourth and fifth generation nursery stock. All exhibit a wide range of leaf variegations. Note reddish to greenish-yellow stems.
Figure 5:
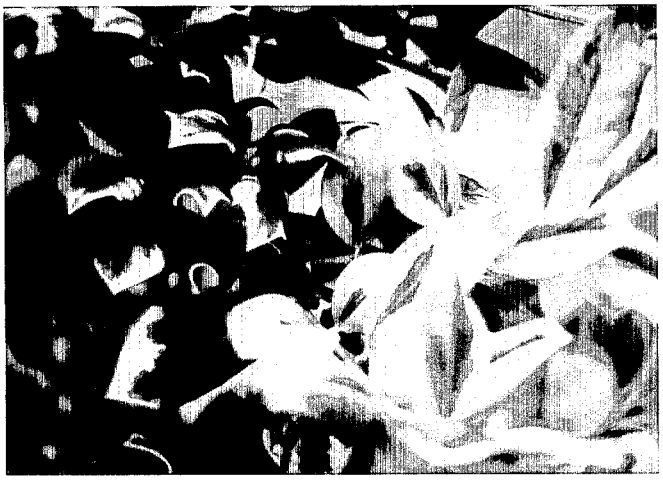
FIG. 5 illustrates the change of color, obvious between first year foliage (right) and the older, more mature foliage (left), toward the center of a field grown plant.
Figure 6:
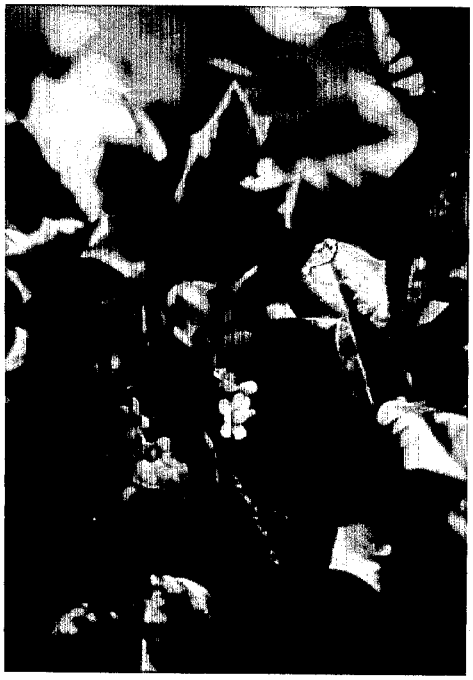
FIG. 6 shows mature second year foliage in spring, with female flowers opening and bronze to peach-yellow new growth emerging just above the flowers on a field grown plant.
Figure 7:
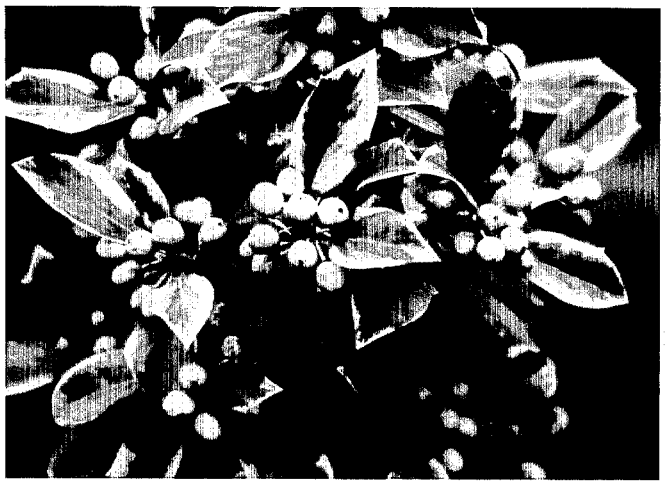
FIG. 7 demonstrates how the berries change to yellow during summer and early fall when exposed to direct sunlight as in center of drawing. Note shaded berries are green to greenish-yellow depending on exposure. Drawing is of a fifth generation field grown progeny under some moisture stress, taken in September, 1991.
Figure 8:
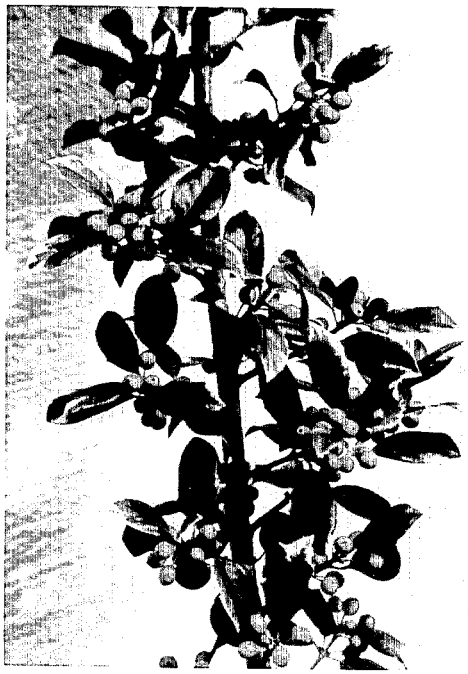
FIG. 8 illustrates the dramatic color change which occurs as cool temperatures cause the fruit to ripen and turn red. Drawing is of same fifth generation field grown plant (FIG. 7) and was taken in late November, 1991.

Ilex×'Hefcup':

Sex: Female.

Habit: Pyramidal, evergreen shrub with a distinct central leader, currently to 5 feet tall in field grown stock of 9 years in age, and should reach a mature height of 18–20' by 8' wide.

TWIGS

First year (juvenile): Leaf bearing only, intense reddish to greenish-yellow on young wood, angular-terete with rounded angles and flattened nodes, becoming more terete with age, 2–5 mm diam.

Second year: Leaf and flower/fruit bearing, slightly darker in color, nearly terete, 4–7 mm diam.

Pubescence: Inconspicuously puberulent, trichomes (vidi 25×) numerous, moderately crowded, white, erect, ca 0.1 mm long, rarely with well scattered trichomes, semi-erect to spreading, to 0.5 mm long.

Lenticels: Inconspicuous, slightly lighter in color than the juvenile twig; conspicuous on second year twigs, raise blister-like pores, arranged in the vertical axis, 1–2 mm long.

LEAVES

Arrangement: Alternate.

Type: Simple.

Duration: Evergreen, persisting several years.

Shape: Variable in shape but generally elliptic-oblong to oblong-rectangular.

Size: 5–8 cm long, 3–4 cm wide.

Margin: Entire to remotely spinose, revolute or with the outer edge of the leaf curving downward near the middle.

Teeth: The lateral spinose teeth are 1–2(3), borne on deltoid projections 1–3 mm long, to 4 mm wide; spine pungent, ca 1 mm long.

One tooth per side: With the lateral spinose teeth usually symmetrical, rarely borne only on one side, commonly borne from near the base to the middle of the leaf.

Two teeth per side: With the lateral spinose teeth commonly symmetrical; one tooth is borne near the leaf apex and one is borne near the base.

Three teeth per side: With the lateral spinose teeth commonly symmetrical one tooth borne near the base and one tooth near the leaf apex with the third tooth borne near the middle of the leaf and projecting downward.

Apex: Spinose-acute to deltoidly spinose-acute, often projecting downward to a 45 degree angle.

Base: Broadly cuneate.

Adaxial surface: Bullate, vaiegated green and yellow, with 5–8 conspicuous pairs of impressed lateral veins and a midrib to 0.5–1 mm wide that is conspicuously yellowish, amongst the green pigmentations; older leaves near center of plant on twigs of three years and older lose the variegation and become dark green, Munsell 7.5 GY ¾ (Wilde & Voigt 1977).

Abaxial surface: Lighter green in color, Munsell 5 GY 5/6–8 (Wilde & Voigt 1977), with lighter variegation patterns, and with lateral veins raised.

Variegation pattern: As discussed above in the DESCRIPTION, the variegation pattern is extremely variable, forming assymetrical patterns on a leaf, often with juvenile leaves exhibiting a solid "peach" yellow, Munsell 2.5Y 6/8 (Wilde & Voigt 1977) to a brighter yellowish color, Munsell 5Y 8/8–10 adaxially and 5Y 8/8–10 abaxially (Wilde & Voigt 1977) on juvenile shoots, and becoming laminated in pattern with colors ranging from yellowish hues, Munsell 2.5Y, 6/6 to 7/6 to 6/8 adaxially (Wilde & Voigt 1977) to greenish hues, Munsell 7.5 GY $\frac{3}{4}$ (Wilde & Voigt 1977), with age; variegation commonly yellowish apical and marginal with green basal and medial, to sometimes interveinal with yellow medially and between the lateral veins.

Stipules: Persistent, inconspicuous, black, isolateral deltoidal, acute, ca. 0.6–0.8 mm long, 0.4–0.6 mm wide.

FLOWERS

Type and location: Congested cymes of few flowers (2–6) borne in leaf axils.

Bracts: Oblong, convex abaxially, broadly acute, 3–6 mm long, 0.6–1 mm wide, micropuberulent.

Pedicels: Subquadrangular, micropuberulent, 4–7 mm long.

Calyx: Rotate, sepals fused basally with 4 green lobes deltoidly navicular with weak keel, spreading, 2 mm long × 1.5–1.7 mm wide.

Corolla: Rotate, petals fused basally with 4 white lobes broadly oblong, obtuse, spreading to ascending, 5.7–6.2 mm long, 2.2–2.5 mm wide.

Stamens: 4, alternating with the petals, presumably staminoids.

*Filaments*—1–1.2 mm long.

*Anthers.*—Basifixed, ca 0.5–0.8 mm long, 0.4–0.6 mm wide.

Pistil: 1, ovary subglobular, ca 1.7–2 mm diam.; style lacking; stigma inconspicuous.

FRUIT

Type: Berry with typically four pyrenes.

Color: Juvenile fruit growing in shade are green, Munsell 2.5 GY 6/8 (Wilde & Voigt 1977), whereas those fruit growing in exposed sunlight are yellowish, Munsell 5Y 8/8–10 (Wilde & Voigt 1977); adult fruit red similar to parent stock, 'Nellie R. Stevens'. Juvenile fruits of 'Nellie R. Stevens' are all green, Munsell 2.5 GY $\frac{5}{8}$ (Wilde & Voigt 1977).

Size: Juvenile fruits exhibiting the yellowish color are ovoid, 0.7–1 cm long, 0.5–0.8 cm wide.

HARDINESS

Three, four and five-year-old field grown Ilex × 'Hefcup' survived a rapid drop in temperature from very mild daytime temperatures (50's F. & 60's F.) in November and December of 1983, to −6 F on Christmas Day (1983). In January 1985, three, four, five and six-year-old progeny of Ilex × 'Hefcup' survived a similar sudden drop in temperature to −8 F. In both instances, some foliage damage was incurred, especially noticeable on the predominantly yellow variegated leaves and solid yellow leaves. The plants made strong new growth in spring and recovered rapidly both years.

HERBARIUM VOUCHERS

Vouchers of the parent plant, the sport, and representative samples of the 3rd–5th generations were obtained with Dr. Paul R. Fantz, Department of Horticultural Science, North Carolina State University, Raleigh, N.C., on Aug. 13, 1991. Vouchers of the flowers were obtained by Randy Hefner on Aug. 26, 1991, and mailed to Paul Fantz for vouchering.

Fantz and Hefner 5240 is a voucher of the 9 foot stock plant, Ilex 'Nellie R. Stevens', with its typical dark green leaves and green fruits. Fantz and Hefner 5241 is a voucher of the variegated sport obtained from the parent 'Nellie R. Stevens' plant. Fantz and Hefner 5242 through 5244 are vouchers of various degrees of foliage variegation of 'Hefcup', representing the 3rd, 5th and 4th generations respectively. Fantz and Hefner 5245 are vouchers of the flowers of 'Hefcup'.

The Munsell Color Charts for Plant Tissues (Wilde & Voigt 1977) was used for the color designations cited with each voucher. All vouchers will be deposited with the Herbarium of the U.S. National Arboretum (NA) in Washington, D.C. upon completion of the patent process.

LITERATURE CITED

Dirr, M. A. 1990. *Manual of Woody Landscape Plants.* 4th ed. Stipes Publ. Co., Champaign, Ill. pp. 417–418.

Liberty Hyde Bailey Hortorium. 1976. *Hortus Third: A Concise Dictionary of Plants Cultivated in the United States and Canada.* Macmillan Publ. Co., New York, N.Y., p. 589.

I claim:

1. Ilex × 'Hefcup' is a new and distinct selection as substantially shown and described herein, a superior selection characterized by a combination of notable characteristics of variegated foliage, yellowish juvenile fruits, lack of variegation reversion in first year growth, and cold hardiness in zone 7.

* * * * *